United States Patent [19]

Cherian

[11] Patent Number: 5,735,829
[45] Date of Patent: Apr. 7, 1998

[54] INTERCOSTAL ANESTHETIC INFUSION CATHETER

[76] Inventor: George Cherian, 6568 High Dr., Prairie Village, Kans. 66208

[21] Appl. No.: 621,101

[22] Filed: Mar. 22, 1996

[51] Int. Cl.$^6$ .................................................. A61M 5/00
[52] U.S. Cl. .................... 604/264; 604/174; 604/280; 604/175
[58] Field of Search ...................... 604/264, 93, 175, 604/280, 174

[56] References Cited

U.S. PATENT DOCUMENTS

| | | | |
|---|---|---|---|
| 2,625,158 | 1/1953 | Lee et al. | 604/93 |
| 3,948,272 | 4/1976 | Guibor | 604/264 |
| 4,380,239 | 4/1983 | Crawford et al. | 604/175 X |
| 4,559,039 | 12/1985 | Ash et al. | 604/175 |
| 5,057,075 | 10/1991 | Moncrief et al. | 604/175 X |

*Primary Examiner*—John D. Yasko
*Attorney, Agent, or Firm*—Kokjer, Kircher, Bowman & Johnson

[57] ABSTRACT

A catheter for applying anesthetic locally to the intercostal nerves of patients who have undergone thoracic surgery. The catheter has a main tube provided with ports which align with the intercostal nerves when the catheter is properly inserted during thoracic surgery. A suture connecting with the catheter tube carries a needle to facilitate threading the catheter through the rib cage area in proximity to each intercostal nerve. The end of the tube opposite the suture carries an adapter which accommodates injection of anesthetic into the catheter. Radiopaque bands are located between the ports so that x-rays can confirm that the catheter remains properly in place.

15 Claims, 1 Drawing Sheet

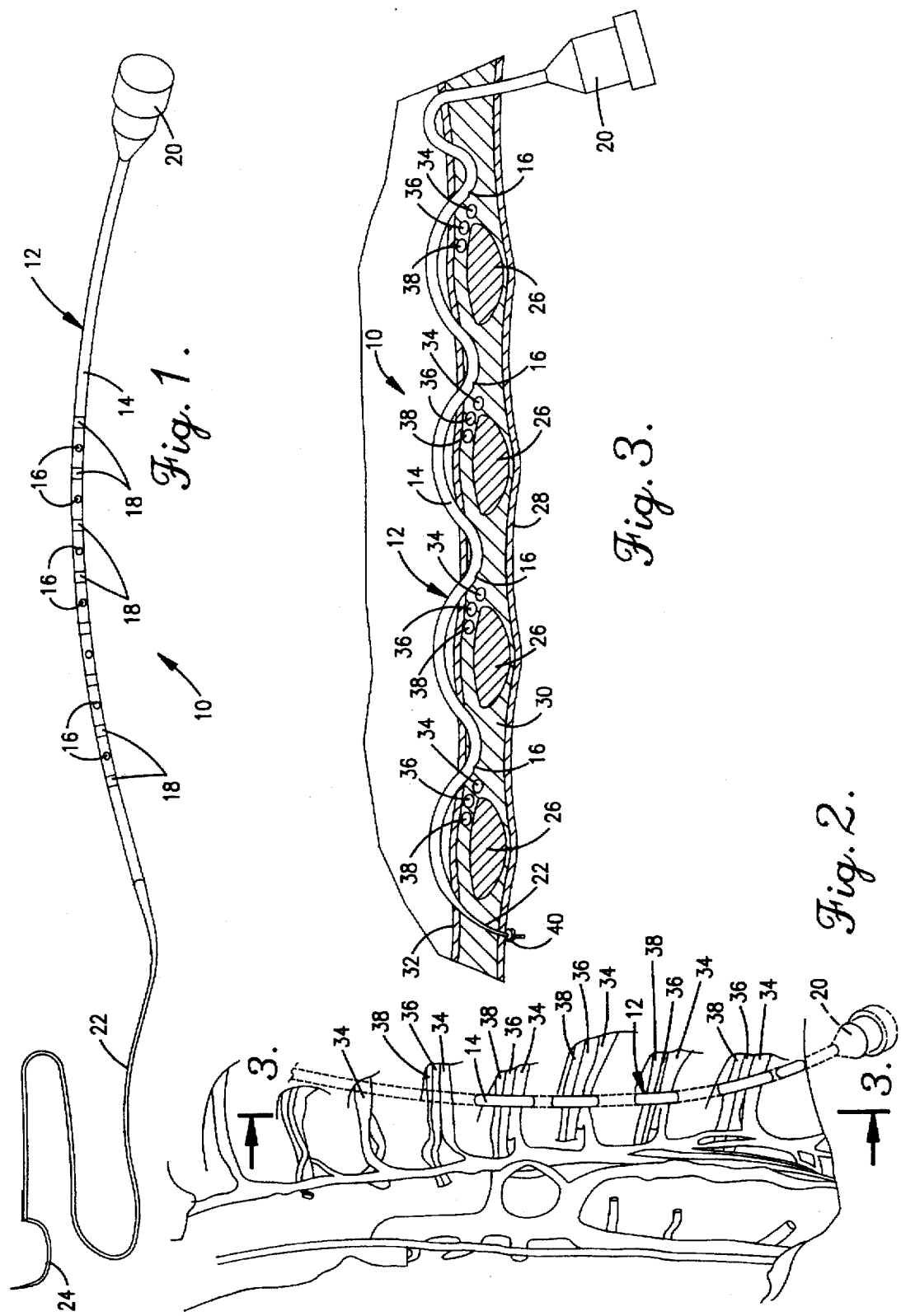

INTERCOSTAL ANESTHETIC INFUSION CATHETER

FIELD OF THE INVENTION

This invention relates generally to the application of local anesthetic to the intercostal nerves and more particularly to a catheter which is specially constructed for insertion during thoracic surgery in order to allow the intercostal nerves to be anesthetized locally after completion of the surgery.

BACKGROUND OF THE INVENTION

Thoracic surgery is one of the more painful procedures in surgery. This pain is mediated by the intercostal nerves. There is a nerve below each rib. These nerves may be injured when the chest is opened either by removing a rib or opening between two ribs or the nerves may be caught when the chest is closed with sutures. During the surgery, the intercostal nerve areas can be locally anesthetized because they are accessible when the chest is opened. However, the anesthetic normally wears off in a matter of about four hours, and the patient then suffers extreme post surgical pain. At that time, the intercostal nerves are no longer accessible because the chest has been closed up, and it is necessary to relieve the pain through the use of morphine, Epidural anesthesia, or other techniques or medications which are much more problematic than is the case with local anesthetics.

SUMMARY OF THE INVENTION

The present invention is directed to a uniquely constructed catheter which can be inserted during thoracic surgery and used after the surgery has been completed to apply anesthetic locally to the intercostal nerve areas. When no longer needed, the catheter can be quickly and easily removed from the patient's body.

In accordance with the invention, a special catheter has a main catheter tube which presents ports for the discharge of anesthetic to the intercostal nerve areas. The ports are spaced apart such that when the catheter is properly placed during the course of thoracic surgery, each port is located adjacent to one of the intercostal nerves that innervates the incisional area. An injection hub or other device for receiving the infusion of anesthetic is provided on one end of the catheter tube and remains outside of the body where it is accessible after the surgery has been completed and the patient's chest has been closed.

A suture or other suitable thread (or an extension of the catheter tube) extends from the other end of the catheter tube and carries a needle on its end. The needle can be threaded through the rib cage area, and the catheter placed near the intercostal nerve. The needle and thread can be used to pull the catheter tube to the proper location where the ports are generally aligned with the intercostal nerves. The end of the thread is pulled outside of the body and may be knotted or otherwise secured to prevent it from being pulled back into the body.

The invention may have radiopaque bands on the catheter tube which mark the locations of the ports. After the operation has been completed, x-ray techniques can be used to provide an indication of the location of the radiopaque markers to make certain that the catheter remains in place to properly locate the catheter ports adjacent to the intercostal nerves. If the catheter tube has been inadvertently displaced from its proper position, either the hub end or the thread end can be pulled until the ports are properly aligned with the intercostal nerves as necessary for effective infusion of the anesthetic. When the catheter is no longer needed, the hub end can be pulled to pull the catheter tube and thread from the chest of the patient.

BRIEF DESCRIPTION OF THE DRAWINGS

In the accompanying drawings which form a part of the specification and are to be read in conjunction therewith and in which like reference numerals are used to indicate like parts in the various views:

FIG. 1 is a perspective view of a catheter constructed in accordance with the present invention for use to infuse anesthetic to intercostal nerve areas following thoracic surgery;

FIG. 2 is a diagrammatic view taken from inside the chest of a patient and showing the catheter of FIG. 1 inserted in the patient; and FIG. 3 is a fragmentary sectional view on an enlarged scale taken generally along line 3—3 of FIG. 2 in the direction of the arrows and showing diagrammatically the proper position of the inserted catheter and the location of the infusion ports relative to the intercostal nerves.

DETAILED DESCRIPTION OF THE INVENTION

Referring now to the drawings in more detail, numeral 10 generally designates a catheter which is constructed according to a preferred embodiment of the present invention and which is used for the infusion of local anesthetic to the areas of intercostal nerves following thoracic surgery. The catheter 10 includes a catheter tube 12 having a tubular wall 14 which defines within it a flow path for anesthetic. The main portion of the catheter tube 12 is provided with a plurality of spaced apart ports 16 which extend through the catheter wall 14 at strategic locations, as will be explained more fully. The tube wall 14 is provided with a plurality of radiopaque bands 18 (or other markings). The bands 18 are preferably located midway between adjacent pairs of the ports 16, with one band 18 spaced beyond each of the endmost ports 16. The configuration of the bands and the ports can vary, and the bands may be over the ports or at any other desired location.

Connected to one end of the catheter tube 12 is a hub or adapter 20. The adapter 20 is constructed to receive a syringe or other delivery system which is used to inject the anesthetic into the catheter 10. The adapter 20 may take any suitable form and may be constructed to be compatible with any type of injection system.

Extending from the end of the catheter tube 12 opposite the hub 20 is a thread which may take the form of a suture 22. The end of the catheter tube from which the suture 22 extends is a closed end, and the suture does not convey the anesthetic. The end of the suture 22 carries a needle 24 which may have a curved shape as illustrated or any other suitable configuration. Instead of a thread or suture, an extension of the catheter itself can be provided and may be preferable from a manufacturing standpoint.

The catheter 10 is inserted into the rib cage area during the course of thoracic surgery when the chest of a patient is open. In FIG. 3, the ribs of the patient are identified by numeral 26, and the skin of the patient is identified by numeral 28. Muscular tissue 30 located in the area of the ribs 26 has an interior lining 32, called the pleura. An intercostal nerve 34 is located beneath the pleura to extend generally along and just below each of the ribs 26. An intercostal artery 36 and an intercostal vein 38 extend in the rib area near each of the intercostal nerves 34.

With continued reference to FIG. 3 in particular, the catheter 10 is inserted into the chest of the patient by first passing the needle through the skin 28, the tissue 30, and the lining 32, preferably at a location displaced slightly from the first intercostal nerve 34 which is to be anesthetized. The needle is then looped back beneath the lining 32 into the tissue 30 near the first intercostal nerve 34 and then back through the lining 32. The needle is successively threaded back through the lining 32 and tissue 30 along a path carrying it in proximity to each of the intercostal nerves 34. When the needle has bypassed the last nerve 34, it is passed through the lining 32, the tissue 30 and the skin 28 back to the exterior of the patient's body.

As the needle is threaded in this fashion through the rib area, the suture 22 follows it and is threaded through the tissue adjacent to each of the intercostal nerves 34, to be anaesthetized. The suture 22 pulls the catheter tube 12 behind it until the tube 12 is properly inserted in the position shown in FIGS. 2 and 3. In this position, the hub 20 remains accessible from the exterior of the patient's body, and the adjacent ports 16 are located in proximity to the adjacent intercostal nerves 34. The needle 24 may be removed from the suture 22, and the suture may be knotted outside of the body and adjacent to the skin 28, as indicated at 40 in FIG. 3. The knot 40 maintains the end of the suture 22 accessible from the exterior of the body and prevents the suture from being inadvertently pulled back inside of the chest area. Other methods to secure the catheter can also be used.

The catheter 10 remains in the inserted position after the chest has been sewn closed. When the anesthetic that was applied to the intercostal nerve areas while the operation was being performed wears out (typically in a matter of about four hours), additional local anesthetic can be applied through the catheter 10 to the intercostal nerves 34. The anesthetic is injected through the adapter 20 into the catheter tube 12 and flows through the catheter tube to the ports 16. Because the ports 16 are located in close proximity to each of the intercostal nerves 34, the anesthetic which flows out of the ports 16 is applied in the immediate vicinity of the intercostal nerves and thus effectively anesthetizes them. Repeated applications of local anesthetic in this manner can be made periodically as long as necessary.

Prior to the infusion of anesthetic through the catheter 10, x-ray or similar equipment can be used to detect the location of the radiopaque bands 18. By noting the location of the bands 18, it can be determined where the ports 16 are located. If the catheter 10 has inadvertently become displaced from its proper position, the suture 22 can be pulled in the area of the knot 40 or the hub 20 can be pulled in order to reposition the catheter in the proper location for application of anesthetic. It is noted that the catheter tube 12 is larger in diameter than the needle 24 and suture 22 so that the catheter tube seals the punctures that are made in the lining 32 as the catheter is being inserted through the tissue 30.

When the catheter 10 is no longer needed, it can be removed from the chest of the patient. This is accomplished by cutting the knot 40 away from the suture 22 and then gently pulling the hub in order to pull the catheter tube and then the suture out of the body.

The catheter 10 may be constructed of any suitable material such as polyethylene, Teflon, Silastic or other materials that are commonly used for catheters. The length and diameter of the catheter tube can vary as desired, as can the number of ports 16 and the spacing between them. It is contemplated that the catheter will be furnished in different styles which have different spacings between adjacent ports 16, in order to accommodate different patients having different distances between adjacent intercostal nerves 34. It is not necessary that each port 16 be located at any particular distance from the adjacent nerve 34; all that is necessary is that the ports be close enough that the anesthetic is effective to anesthetize the nerves.

It is thus apparent that the catheter 10 allows anesthetic to be applied locally to the intercostal nerves 34 following the completion of thoracic surgery when the chest of the patient has been closed. Consequently, there is no need to use problematic anesthetic procedures such as the use of large doses of morphine or Epidural anesthetics in order to relieve the extreme pain normally suffered by patients who have undergone thoracic surgery.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative, and not in a limiting sense.

Having thus described the invention, I claim:

1. A catheter for applying post-surgical anesthetic locally to spaced apart intercostal nerves of a patient, said catheter comprising:

a catheter tube for insertion in the body of the patient at a selected location extending in proximity to the intercostal nerves, said catheter tube having opposite ends and a tubular wall defining a flow passage for the anesthetic;

a plurality of ports through said tubular wall for discharging the anesthetic from the catheter tube, said ports being spaced apart in an arrangement locating adjacent ports in proximity to adjacent intercostal nerves when the catheter tube is inserted to said selected location;

means on one end of said catheter tube for receiving the anesthetic and directing it to the tube, said one end being outside the body of the patient when the catheter tube is inserted to said selected location;

a thread element on the other end of said catheter tube for pulling said tube to said selected location; and a needle on said thread element to accommodate threading of the thread element through the body of the patient.

2. A catheter as set forth in claim 1, including means on said tube for indicating the locations of said ports.

3. A catheter as set forth in claim 1, including indicating means on said tube providing indications of the port locations from the exterior of the body of the patient.

4. A catheter as set forth in claim 1, including a plurality of radiopaque markings on said tube providing indications of the port locations.

5. A catheter as set forth in claim 4, wherein each marking comprises a radiopaque band having a preselected location relative to the ports.

6. A catheter as set forth in claim 1, wherein said thread element is accessible from the exterior of the body of the patient to allow the catheter tube to be repositioned from the exterior of the body.

7. A catheter for infusing a local anesthetic to spaced apart intercostal nerves of a patient undergoing thoracic surgery, said catheter comprising:

a catheter tube having opposite ends and a tubular wall presenting a plurality of ports therethrough spaced apart to situate adjacent ports in proximity to adjacent intercostal nerves when the catheter tube is at a selected location in the body of the patient;

means on one end of said catheter tube for receiving the anesthetic and directing it to said tube, said means being accessible from the exterior of the body when the tube is in said selected location; and needle and thread means connected with the other end of said catheter tube for situating said tube at said selected location.

8. A catheter as set forth in claim 7, including means on said tube for indicating the locations of said ports.

9. A catheter as set forth in claim 7, including indicating means on said tube providing indications of the port locations from the exterior of the body of the patient.

10. A catheter as set forth in claim 7, including a plurality of radiopaque markings on said tube providing indications of the port locations.

11. A catheter as set forth in claim 10, wherein each marking comprises a radiopaque band located between adjacent ports.

12. A catheter as set forth in claim 7, wherein said needle and thread means comprises:

a thread element extending from said other end of the catheter tube; and a needle on said thread element to accommodate threading of the thread element and tube through the body to said selected location of the tube.

13. A catheter as set forth in claim 12, wherein said thread element is accessible from the exterior of the body of the patient to allow the catheter tube to be repositioned from the exterior of the body.

14. A catheter for applying a local anesthetic to intercostal nerves in a patient who has undergone thoracic surgery, said catheter comprising:

a catheter tube having opposite ends and a tubular wall presenting a plurality of ports therethrough, said ports having locations on the tube to be brought into general alignment with the intercostal nerves when the catheter tube is inserted in the patient at a selected location;

means on one end of said tube accessible from the exterior of the patient for receiving anesthetic and directing it through said tube;

a thread element on the other end of said tube for pulling the tube to said selected location;

a needle on said thread element to facilitate pulling the thread through the body of the patient; and radiopaque marking means on said tube detectable from the exterior of the patient to provide an indication of the location of said ports relative to the intercostal nerves.

15. A catheter as set forth in claim 14, wherein said marking means comprises a plurality of radiopaque markers on the tube located between adjacent ports.

* * * * *